United States Patent [19]

Merger et al.

[11] 4,158,017
[45] Jun. 12, 1979

[54] PREPARATION OF 1,3-DIAMINO-2,2-DIMETHYL-PROPANE

[75] Inventors: Franz Merger, Frankenthal; Adolph Segnitz, Bad Durkheim, both of Fed. Rep. of Germany

[73] Assignee: BASF Aktiengesellschaft, Fed. Rep. of Germany

[21] Appl. No.: 901,194

[22] Filed: Apr. 28, 1978

[30] Foreign Application Priority Data

May 20, 1977 [DE] Fed. Rep. of Germany ....... 2722957

[51] Int. Cl.$^2$ .................. C07C 85/06; C07C 85/08
[52] U.S. Cl. ............... 260/585 B; 260/583 P; 260/584 R; 260/585 C
[58] Field of Search ................. 260/585 B, 585 C

[56] References Cited

U.S. PATENT DOCUMENTS

| 2,477,943 | 8/1949 | Robinson et al. | 260/585 C |
|---|---|---|---|
| 2,636,902 | 4/1953 | Taylor et al. | 260/585 B |
| 3,520,933 | 7/1970 | Adam et al. | 260/585 B |
| 4,078,003 | 3/1978 | Feichtinger et al. | 260/583 P |

Primary Examiner—Patrick Garvin
Assistant Examiner—John Doll
Attorney, Agent, or Firm—Keil & Witherspoon

[57] ABSTRACT 1,3-Diamino-2,2-dimethyl-propane is prepared by reacting hydroxypivalaldehyde with ammonia and hydrogen in the presence of a nickel catalyst at from 40° to 150° C. and thereafter at from 220° to 300° C. The product is a starting material for the manufacture of dyes, crop protection agents and plastics, especially nylons and polyurethanes.

12 Claims, No Drawings

PREPARATION OF 1,3-DIAMINO-2,2-DIMETHYL-PROPANE

The present invention relates to a process for the preparation of 1,3-diamino-2,2-dimethyl-propane by reacting hydroxypivalaldehyde with ammonia and hydrogen in the presence of a nickel catalyst at from 40 to 150° C. and thereafter at from 220° to 300° C.

German Published Application DAS No. 2,358,355 discloses that the reaction of neopentylglycol with ammonia and hydrogen at from 220° to 300° C. under a pressure of at least 10 atmospheres, in the presence of a catalyst which contains from 23 to 60 percent by weight of nickel precipitated on a carrier and may or may not contain from 16 to 40 percent by weight of chromium, gives 1,3-diamino-2,2-dimethyl-propane. It is advantageous to use a reaction temperature of from 240° to 260° C. and a catalyst which contains some chromium in addition to nickel. The catalyst must be a supported catalyst. As is shown by the Examples, 1-amino-3-hydroxy-2,2-dimethyl-propane, in a yield of from 6.2 to 21.8 percent, is formed as a by-product of the reaction. This by-product must be recycled (column 4, lines 40 to 46) and only undergoes amination in a second reaction. It is pointed out (column 1, lines 55 to 66) that only by conforming to the above conditions did it prove possible to obtain 1,3-diamino-2,2-dimethyl-propane in substantial yield. In the case of neopentylglycol, which is more stable than propane-1,3-diol, dehydration by β-elimination cannot occur, but hydroxypivalaldehyde can form by dehydrogenation of a hydroxymethyl group to give an aldehyde group. Further, an aldol cleavage to give formaldehyde and isobutyraldehyde would be expected. The fragments thereby produced could then react with the ammonia and hydrogen present in the reaction mixture, to form methylamine and isobutylamine by reductive amination (column 1, lines 56 to 66).

We have found that 1,3-diamino-2,2-dimethyl-propane is obtained in an advantageous manner when hydroxypivalaldehyde is reacted with ammonia and hydrogen in the presence of a nickel catalyst, at from 40° to 150° C. in a first step, and thereafter at from 220° to 300° C. in a second step.

The reaction can be represented by the following equation:

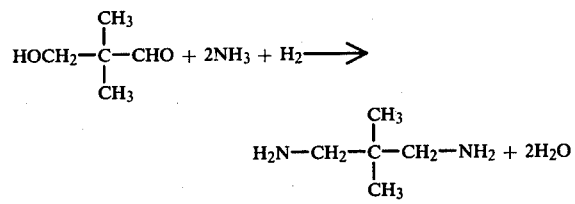

Compared to the prior art, the process of the invention gives 1,3-diamino-2,2-dimethyl-propane more simply and more economically, in better yield and greater purity. The synthesis of neopentylglycol from hydroxypivalaldehyde becomes unnecessary. These advantageous results are surprising in view of the above publication, the catalysts used, which generally are unsupported, and the reaction conditions employed according to the invention. Substantially greater redissociation of the starting material to give formaldehyde and isobutyraldehyde, with subsequent formation of methylamine and isobutylamine, would have been expected. Equally, it was not to be expected that a 2-step reaction, with one step carried out at a low temperature, would even give a better yield of the 1,3-diamino compound.

The first step of the reaction is carried out at from 40° to 150° C., preferably from 60° to 100° C., and the second step at from 220° to 300° C., especially from 240° to 260° C., under atmospheric pressure or, as a rule, under superatmospheric pressure, preferably of from 5 to 500 bars, and especially from 50 to 320 bars, in the first step advantageously at from 50 to 150 bars, and especially from 90 to 120 bars, and in the second step advantageously at from 200 to 320 bars and especially from 250 to 300 bars, batchwise or, as a rule, advantageously by continuous operation. Advantageously, no additional solvent is used. The first step of the reaction is generally carried out for from 0.5 to 5, preferably from 0.75 to 3.5, and especially from 1 to 2.5 hours, and the second step generally for from 1 to 10, preferably from 2 to 8, and especially from 3 to 5, hours.

As a rule it is advantageous to use unsupported nickel catalysts. Preferred hydrogenation catalysts are unsupported catalysts which contain only one metal, namely nickel, for example appropriate sintered catalysts. The nickel in the catalyst may be in the form of an oxide and/or may be mixed with phosphoric acid. The hydrogenation catalyst is as a rule used for the reaction in an amount of from 0.5 to 50 percent by weight, preferably from 5 to 50 percent by weight, and especially from 10 to 25 percent by weight, based on hydroxypivalaldehyde. As a rule, hydrogen is supplied to the reaction mixture, both at the start and in the course of the reaction, in such amount that the reaction pressure at the reaction temperature always assumes an appropriate value, advantageously conforming to the above values. Inert gases, eg. nitrogen, may also be used in order to set up the appropriate pressure. The use of Raney nickel is preferred. The hydrogen is generally used in excess over the starting material II. Advantageously, the reaction is carried out at a hydrogen partial pressure of from 40 to 200 bars, preferably from 50 to 100 bars, in general with from 4 to 40, preferably from 5 to 20, moles of hydrogen per mole of hydroxypivalaldehyde. The hydrogen may be fed to the reaction batchwise, or advantageously, continuously and/or the catalyst itself can be freshly charged with hydrogen after a given reaction time.

Ammonia can be used in the form of a solution, advantageously an aqueous solution, or advantageously in the form of gaseous or liquid ammonia. As a rule, from 5 to 100, preferably from 5 to 60, and especially from 10 to 60, moles of ammonia are used per mole of hydroxypivalaldehyde.

The reaction may be carried out as follows: in the first step, a mixture of hydroxypivalaldehyde, hydrogen and ammonia, together with the hydrogenation catalyst, is kept in a reactor for the appropriate reaction time at the reaction temperature and the reaction pressure of the first step and thereafter under the above conditions of temperature, time and pressure for the second step. The reaction mixture is then cooled, and filtered, with or without addition of a solvent, eg. ethanol, before filtration. The end product I may be isolated from the filtrate in accordance with the conventional methods, for example by evaporating the filtrate and fractionally distilling the residue.

1,3-Diamino-2,2-dimethyl-propane, obtainable by the process of the invention, is a valuable starting material for the manufacture of dyes, crop protection agents and plastics, especially nylons and polyurethanes. With regard to its use, reference may be made to German Published Application DAS 2,358,355 and to J. Polym. Sci. 40 (1959), 359-366.

In the Examples, parts are by weight and bear the same relation to parts by volume as that of the kilogram to the liter.

EXAMPLE

400 Parts of hydroxypivalaldehyde, 120 parts of moist Raney nickel (containing 100 parts of pure nickel) and 1,200 parts by volume of ammonia are introduced into a shaking autoclave. The mixture is heated to 90° C. in the course of 180 minutes and hydrogen up to a pressure of 100 bars is forced in. The mixture is left for 2 hours at 90° C. with additional hydrogen (up to 20 bars) being charged in during the reaction in order to maintain the pressure of 100 bars. The mixture is then heated to 250° C. in the course of 240 minutes and the pressure is brought to 300 bars with hydrogen. The mixture is then kept for 4 hours at 250° C. and 300 bars pressure, whilst vigorously shaking the autoclave, with additional introduction of up to 20 bars of hydrogen. After cooling and letting down the autoclave, the mixture is filtered. According to analysis by gas chromatography, 335 parts of 1,3-diamino-2,2-dimethyl-propane (83.8% of theory) of boiling point 60°-62° C./26 mm Hg and 46 parts of isobutylamine (16.1% of theory) are obtained.

We claim:

1. A process for the preparation of 1,3-diamino-2,2-dimethylpropane, wherein hydroxypivalaldehyde is reacted with ammonia and hydrogen in the presence of a nickel catalyst, at from 40° to 150° C. in a first step, and thereafter at from 220° to 300° C. in a second step.

2. A process as claimed in claim 1, wherein the first step of the reaction is carried out at from 60° to 110° C.

3. A process as claimed in claim 1, wherein the second step of the reaction is carried out at from 240° to 260° C.

4. A process as claimed in claim 1, wherein the reaction is carried out under a pressure of from 5 to 500 bars.

5. A process as claimed in claim 1, wherein the reaction is carried out under a pressure of from 50 to 320 bars.

6. A process as claimed in claim 1, wherein the first step of the reaction is carried out under a pressure of from 50 to 150 bars.

7. A process as claimed in claim 1, wherein the second step of the reaction is carried out under a pressure of from 200 to 320 bars.

8. A process as claimed in claim 1, wherein the first step of the reaction is carried out for from 0.5 to 5 hours.

9. A process as claimed in claim 1, wherein the second step of the reaction is carried out for from 1 to 10 hours.

10. A process as claimed in claim 1, wherein the reaction is carried out with from 0.5 to 50 percent by weight of the hydrogenation catalyst, based on hydroxypivalaldehyde.

11. A process as claimed in claim 1, wherein the reaction is carried out under a partial pressure of hydrogen of from 40 to 200 bars.

12. A process as claimed in claim 1, wherein the reaction is carried out with from 5 to 100 moles of ammonia per mole of hydroxypivalaldehyde.

* * * * *